US00PP20287P2

(12) United States Plant Patent
Bolwell

(10) Patent No.: US PP20,287 P2
(45) Date of Patent: Sep. 8, 2009

(54) ***GAZANIA* PLANT NAMED 'SUGA402'**

(50) Latin Name: *Gazania hybrida*
Varietal Denomination: SUGA402

(75) Inventor: Narelle Gai Bolwell, Picton (AU)

(73) Assignee: Nuflora International Pty. Ltd., Macquarie Fields, NSW (AU)

( * ) Notice: Subject to any disclaimer, the term of this patent is extended or adjusted under 35 U.S.C. 154(b) by 0 days.

(21) Appl. No.: 12/152,676

(22) Filed: May 14, 2008

(51) Int. Cl.
*A01H 5/00* (2006.01)

(52) U.S. Cl. ..... Plt./334
(58) Field of Classification Search ..... Plt./334
See application file for complete search history.

*Primary Examiner*—Susan B McCormick Ewoldt
(74) *Attorney, Agent, or Firm*—C. A. Whealy

(57) ABSTRACT

A new and distinct cultivar of *Gazania* plant named 'SUGA402', characterized by its compact, outwardly spreading, low-growing and mounded plant habit; freely branching growth habit; freely flowering habit; large anemone-type inflorescences with dark orange-colored ray florets; and good garden performance.

1 Drawing Sheet

Botanical designation: *Gazania hybrida.*
Cultivar denomination: 'SUGA402'.

BACKGROUND OF THE INVENTION

The present invention relates to a new and distinct cultivar of *Gazania* plant, botanically known as *Gazania hybrida* and hereinafter referred to by the name 'SUGA402'.

The objective of the breeding program is to create new *Gazania* cultivars with desirable and unique inflorescence form and floret colors.

The new *Gazania* originated from a cross-pollination in Picton, New South Wales, Australia in December, 2003, of a proprietary selection of *Gazania hybrida* identified as code number X02.1.21, not patented, as the female, or seed, parent with a proprietary selection of *Gazania hybrida* identified as code number X01.1.7, as the male, or pollen, parent. The new *Gazania* was discovered and selected by the Inventor as a single flowering plant within the progeny of the stated open-pollination in a controlled greenhouse environment Cobbitty, New South Wales, Australia in October, 2004.

Asexual reproduction of the new *Gazania* by vegetative tip cuttings in a controlled greenhouse environment in Cobbitty, New South Wales, Australia since October, 2004, has shown that the unique features of this new *Gazania* are stable and reproduced true to type in successive generations.

SUMMARY OF THE INVENTION

Plants of the new *Gazania* have not been observed under all possible environmental conditions. The phenotype may vary somewhat with variations in environment such as temperature and light intensity, without, however, any variance in genotype.

The following traits have been repeatedly observed and are determined to be the unique characteristics of the new *Gazania.* These characteristics in combination distinguish 'SUGA402' as a new and distinct cultivar of *Gazania:*

1. Compact, outwardly spreading, low-growing and mounded plant habit.
2. Freely branching growth habit.

3. Freely flowering habit.
4. Large anemone-type inflorescences with dark orange-colored ray florets.
5. Good garden performance.

Plants of the new *Gazania* differ from plants of the female parent selection primarily in ray floret color as plants of the female parent selection have light red-colored ray florets. Plants of the new *Gazania* differ from plants of the male parent selection primarily in inflorescence form as plants of the male parent selection have daisy-type inflorescences.

Plants of the new *Gazania* can be compared to plants of the *Gazania* 'SUGA119', disclosed in U.S. Plant Pat. No. 18,418. In side-by-side comparisons conducted in Cobbitty, New South Wales, Australia, plants of the new *Gazania* differed primarily from plants of 'SUGA119' in ray floret coloration as plants of 'SUGA119' had orange-colored ray florets.

BRIEF DESCRIPTION OF THE PHOTOGRAPHS

The accompanying photographs illustrate the overall appearance of the new *Gazania.* These photographs show the colors as true as it is reasonably possible to obtain in colored reproductions of this type. Colors in the photographs may differ slightly from the color values cited in the detailed botanical description which accurately describe the colors of the new *Gazania.*

The photograph on at the bottom of the sheet comprises a side perspective view of a typical flowering plant of 'SUGA402' grown in a container.

The photograph at the top of the sheet is a close-up view of typical inflorescences and leaves of 'SUGA402'.

DETAILED BOTANICAL DESCRIPTION

The aforementioned photographs and following observations and measurements describe plants grown during the late winter and early spring in Encinitas, Calif. and under conditions and practices which approximate those generally used in commercial potted *Gazania* production. Plants were grown in 10-cm containers in a polyethylene-covered greenhouse for 13 weeks. During the production of the plants, day temperatures averaged 27° C., night temperatures averaged 16° C. and light levels averaged 4,000 foot-candles. In the following description, color references are made to The Royal Horticultural Society Colour Chart, 1995 Edition, except where general terms of ordinary dictionary significance are used.

Botanical classification: *Gazania hybrida* 'SUGA402'.

Parentage:

*Female, or seed, parent.*—Proprietary selection of *Gazania hybrida* identified as code number X02.1.21, not patented.

*Male, or pollen, parent.*—Proprietary selection of *Gazania hybrida* identified as code number X01.1.7, not patented.

Propagation:

*Type.*—Terminal cuttings.

*Time to initiate roots, summer.*—About ten days at temperatures of about 20° C.

*Time to initiate roots, winter.*—About twelve days at temperatures of about 18° C.

*Time to produce a rooted young plant, summer.*—About 38 days at temperatures of about 20° C.

*Time to produce a rooted young plant, winter.*—About 42 days at temperatures of about 18° C.

*Root description.*—Fibrous, medium in thickness; white in color.

*Rooting habit.*—Freely branching; dense.

Plant description:

*Appearance/form.*—Herbaceous anemone-type potted *Gazania*. Compact, outwardly spreading, low-growing and mounded plant habit. Strong and freely branching growth habit with about twelve lateral branches per plant. Vigorous growth habit.

*Plant height.*—About 18 cm.

*Plant width.*—About 26 cm.

*Lateral branches.*—Length: About 11 cm. Diameter: About 5 mm. Internode length: About 6 mm. Strength: Strong. Texture: Scattered pubescence. Color: Close to 147C tinted with close to 182C.

Foliage description:

*Arrangement.*—Alternate, simple.

*Length.*—About 7.2 cm.

*Width.*—About 4.8 cm.

*Shape.*—Deeply dissected with five to nine lobes.

*Apex.*—Broadly acute to obtuse.

*Base.*—Obtuse.

*Margin.*—Deeply indented; entire.

*Texture, upper surface.*—Smooth, glabrous.

*Texture, lower surface.*—Pubescent.

*Venation pattern.*—Pinnate.

*Color.*—Developing foliage, upper surface: Close to 137B. Developing foliage, lower surface: Close to 155D. Fully expanded foliage, upper surface: Close to 147A; venation, close to 147C. Fully expanded foliage, lower surface: Close to 191C to 191D; venation, close to 148C.

*Petiole length.*—About 10 cm.

*Petiole diameter.*—About 5 mm.

*Petiole texture, upper and lower surfaces.*—Smooth, glabrous.

*Petiole color, upper and lower surfaces.*—Close to 147C.

Inflorescence description:

*Appearance.*—Anemone-type inflorescence form with elliptical-shaped ray florets. Inflorescences borne on terminals above foliage. Disc and ray florets arranged acropetally on a capitulum. Inflorescences not fragrant.

*Flowering season.*—Plants flower from spring to early fall in Southern California; flowering continuous during this period.

*Inflorescence longevity.*—Inflorescences last about one week on the plant; inflorescences persistent.

*Quantity of inflorescences.*—About 14 inflorescences develop per plant.

*Inflorescence bud.*—Height: About 3.5 cm. Diameter: About 2 cm. Shape: Ovoid. Color: Close to 165B to 165C.

*Inflorescence size.*—Diameter: About 9 cm. Depth (height): About 2.8 cm. Diameter of disc: About 3.5 cm to 4 cm. Receptacle height: About 1.8 cm. Receptacle diameter: About 2.8 cm. Receptacle color: Close to 146A.

*Ray florets.*—Shape: Elliptical. Orientation: Initially upright, then about 30° from vertical, outer ray florets perpendicular to peduncle; eventually reflexing. Length: About 4.7 cm. Width: About 1 cm. Apex: Acute or emarginate. Base: Acute. Margin: Entire. Texture, upper and lower surfaces: Smooth, glabrous; longitudinally ribbed. Number of ray florets per inflorescence: About 18 in one to two whorls. Color: When opening, upper surface: Close to 171B. When opening, lower surface: Close to 174D. Fully opened, upper surface: Ground color, close to 172A; towards the base, brownish spot, close to 177A; at the base, orange "v"-shape area, close to 25A. With development, apices fade to close to 169B. Fully opened, lower surface: Ground color, close to 171C; thin longitudinal stripes, close to 168D; at the base, close to 167D.

*Disc florets.*—Arrangement: Massed at center of receptacle. Shape: Tubular, elongated, enlarged. Apex: Five-pointed. Length: About 2.5 cm. Width: About 4 mm. Number of disc florets per inflorescence: About 220. Color, immature: Apex: Close to 163A. Mid-section: Close to 166C. Base: Close to 157B. Color, mature: Apex: Close to 21B. Mid-section: Close to 171A. Base: Close to 157B.

*Phyllaries.*—Number of phyllaries per inflorescence: About 40 in about two whorls. Length: About 8 mm to 10 mm. Width: About 2 mm. Shape: Lanceolate. Apex: Acuminate. Base: Fused. Margin: Entire. Texture, upper surface: Smooth, glabrous. Texture, lower surface: Minute scattered pubescence. Color, upper surface: Close to 146C. Color, lower surface: Close to 146B.

*Peduncles.*—Length: About 15.6 cm. Diameter: About 3 mm. Angle: Upright to about 30° to 45° from vertical. Strength: Strong. Texture: Scattered pubescence. Color: Close to 145A.

*Reproductive organs.*—Androecium: Only observed on disc florets. Stamens per floret: About five. Filament length: About 5 mm. Filament color: Close to 157D. Anther shape: Lanceolate to acicular. Anther length: About 3.5 mm. Anther color: Close to 23C. Pollen amount: None observed. Gynoecium: Only observed on disc florets. Pistil length: About 1.4 cm. Stigma shape: Two-parted. Stigma color: Close to 164B. Style length: About 9 mm. Style color: Close to 164C. Ovary color: Close to 157D.

*Seed/fruit.*—Seed and fruit production has not been observed.

Disease/pest resistance: Resistance to pathogens and pests common to *Gazanias* has not been observed on plants grown under commercial conditions.

Garden performance: Plants of the new *Gazania* have been observed to have good garden performance and to tolerate wind, rain and temperatures from about 2° C. to about 35° C.

It is claimed:

1. A new and distinct *Gazania* plant named 'SUGA402' as illustrated and described.

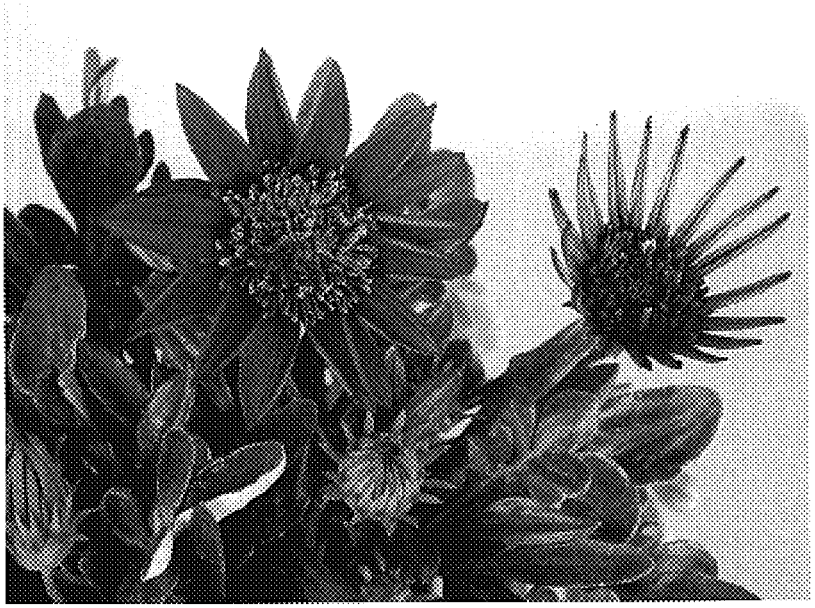
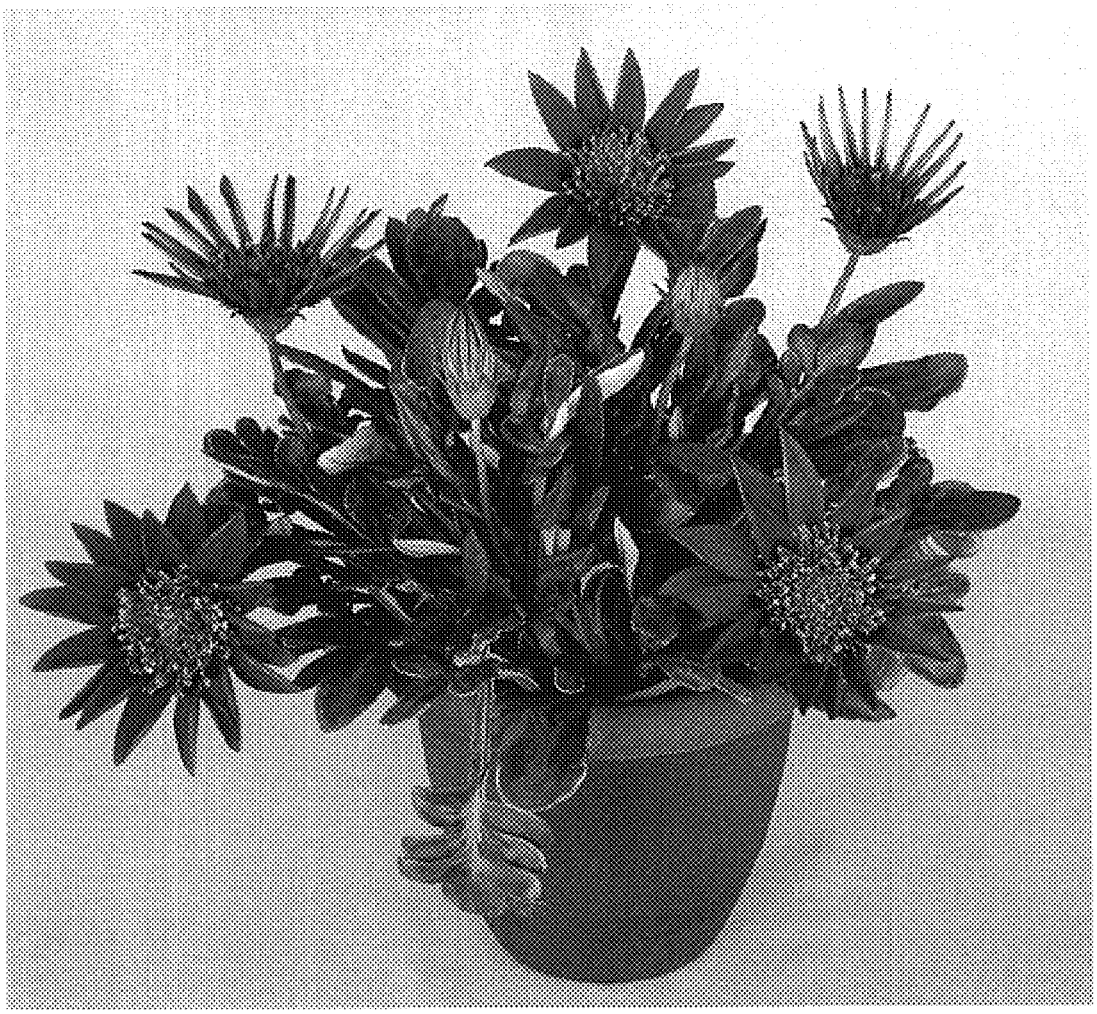

* * * * *